United States Patent [19]

Johnson et al.

[11] 4,337,204
[45] Jun. 29, 1982

[54] PGI₂ LOWER ALKYL ESTERS

[75] Inventors: Roy A. Johnson, Kalamazoo; Frank H. Lincoln, Portage; John E. Pike, Kalamazoo, all of Mich.

[73] Assignee: The Upjohn Company, Kalamazoo, Mich.

[21] Appl. No.: 248,637

[22] Filed: Mar. 27, 1981

Related U.S. Application Data

[63] Continuation of Ser. No. 819,940, Jul. 28, 1977, which is a continuation-in-part of Ser. No. 725,550, Sep. 22, 1976, abandoned, which is a continuation-in-part of Ser. No. 716,770, Aug. 23, 1976, abandoned.

[51] Int. Cl.³ .......................................... C07D 307/935
[52] U.S. Cl. ..................................................... 549/465
[58] Field of Search ................................... 260/346.22

[56] References Cited

PUBLICATIONS

Moncada et al., Prostaglandins, vol. 12, pp. 658–713, (1976).

Primary Examiner—Henry R. Jiles
Assistant Examiner—Bernard Dentz
Attorney, Agent, or Firm—Robert A. Armitage

[57] ABSTRACT

The present invention relates to PGI₂ lower alkyl esters, having pharmacological activity. Particularly, the compounds described herein are useful as platelet aggregation inhibitors.

3 Claims, No Drawings

PGI₂ LOWER ALKYL ESTERS

CROSS REFERENCE TO RELATED APPLICATIONS

This application is a continuation of co-pending application Ser. No. 819,940, filed July 28, 1977; which is a continuation-in-part of Ser. No. 725,550, filed Sept. 22, 1976, now abandoned; which was a continuation-in-part of Ser. No. 716,770, filed Aug. 23, 1976, now abandoned.

BACKGROUND OF THE INVENTION

The present invention relates to novel compositions of matter which are derivatives of prostacyclin or PGI₂. The chemical name for prostacyclin is (5Z)-5,6-didehydro-9-deoxy-6,9α-epoxy-PGF₁α. Specifically the present invention relates to PGI₂ lower alkyl esters.

Prostacyclin itself was first reported as "PGX" by Moncada and his co-workers. See Moncada, et al., Prostaglandins 12:658-713 (1976). Prostacyclin is a circulating hormone in the arterial circulation of mammals. See "Prostacyclin As A Circulating Hormone", Nature 273:767-768 (29 June 1978) and Grycleweski, R. J., et al., "Generation of Prostacyclin By Lungs In Vivo And Its Release Into Arterial Circulation", Nature 273:765-767 (29 June 1978).

PRIOR ART

Subsequent to any invention described herein the existence of prostacyclin as a naturally-occurring composition of matter was reported in the aforementioned references.

SUMMARY OF THE INVENTION

The present invention relates to a compound of the formula

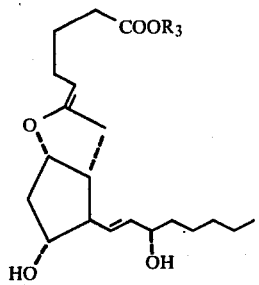

or a mixture comprising that compound and the enantiomer thereof, wherein R₃ is alkyl of one to 4 carbon atoms, inclusive; including the lower alkanoates thereof.

Compounds in accordance with the present invention are prepared by chemical methods and have pharmacological uses as are described in U.S. Pat. No. 4,158,667, incorporated here by reference. Accordingly, compounds in accordance with the present invention are useful for a variety of pharmacological purposes. Accordingly, the compounds in accordance with the present invention are especially useful whenever it is desired to inhibit platelet aggregation, to reduce the adhesive character of platelets, and to remove or prevent the formation of thrombi in mammals, including man. For example, these compounds are useful in the treatment and prevention of myocardial infarcts, to treat and prevent post-operative thrombosis, to promote patency of vascular drafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long-term prophylaxis following myocardial infarcts and strokes. For these purposes, the compounds are administered systemically, e.g., intravenously, subcutaneously, intramuscularly, and in the form of sterile implants for prolonged action. For rapid response, especially in emergency situations, the intravenous route of administration is preferred. Dosages in the range about 0.01 to about 10 mg/kg of body weight per day are used, the exact dose depending on the age, weight, and condition of the patient or animal, and on the frequency and route of administration.

The addition of these compounds to whole blood provides in vitro applications, such as storage of whole blood to be used in heart-lung machines. Additionally, whole blood containing these compounds can be circulated through limbs and organs, e.g., heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused whole body, attached or detached, to the recipient, or to two or all of those at a total steady state dose of about 0.001-1.0 μg/ml of whole blood. These compounds are also useful in preparing platelet-rich concentrates from blood for use in treating thrombocytopenia or in chemotherapy.

DESCRIPTION OF THE PREFERRED EMBODIMENTS

The present invention particularly relates to:
(5Z)-9-Deoxy-6,9α-epoxy-Δ⁵-PGF₁, methyl ester; and
(5Z)-9-Doexy-6,9α-epoxy-Δ⁵-PGF₁, methyl ester, 11,15-diacetate.

We claim:
1. A compound of the formula

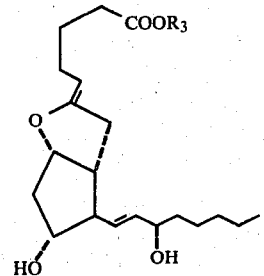

or a mixture comprising that compound and the enantiomer thereof, wherein R₃ is alkyl of one to 4 carbon atoms, inclusive; including the lower alkanoates thereof.

2. (5Z)-9-Deoxy-6,9α-epoxy-Δ⁵-PGF₁, methyl ester, a compound according to claim 1.

3. (5Z)-9-Deoxy-6,9α-epoxy-Δ⁵-PGF₁, methyl ester, 11,15-diacetate, a compound according to claim 1.